US008496607B2

(12) United States Patent
Feng et al.

(10) Patent No.: US 8,496,607 B2
(45) Date of Patent: Jul. 30, 2013

(54) MULTI-LUMEN CATHETER

(75) Inventors: Brian Pak-Yun Feng, Bloomington, IN (US); Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 726 days.

(21) Appl. No.: 12/631,461

(22) Filed: Dec. 4, 2009

(65) Prior Publication Data
US 2011/0137225 A1 Jun. 9, 2011

(51) Int. Cl.
*A61M 37/00* (2006.01)

(52) U.S. Cl.
USPC ........................................................ 604/6.16

(58) Field of Classification Search
USPC .................. 604/4.01, 6.16, 43, 280, 283, 284
See application file for complete search history.

(56) References Cited

U.S. PATENT DOCUMENTS

| 3,938,530 A | 2/1976 | Santomieri ............... 128/349 R |
| 3,946,741 A | 3/1976 | Adair ............................ 128/347 |
| 4,129,129 A | 12/1978 | Amrine ..................... 128/214 R |
| 4,134,402 A | 1/1979 | Mahurkar ................. 128/214 R |
| 4,154,242 A | 5/1979 | Termanini ................. 128/349 R |
| 4,493,696 A | 1/1985 | Uldall ............................. 604/43 |
| RE31,855 E | 3/1985 | Osborne |
| 4,568,329 A | 2/1986 | Mahurkar ....................... 604/43 |
| 4,581,025 A | 4/1986 | Timmermans ................ 604/264 |
| 4,583,968 A | 4/1986 | Mahurkar ....................... 604/43 |
| 4,643,711 A | 2/1987 | Bates ............................... 604/4 |
| 4,655,745 A | 4/1987 | Corbett ........................... 604/49 |
| 4,680,029 A | 7/1987 | Ranford et al. ............... 604/280 |
| 4,733,669 A | 3/1988 | Segal ............................. 128/663 |
| 4,769,005 A | 9/1988 | Ginsburg et al. ............... 604/53 |
| 4,772,268 A | 9/1988 | Bates ............................. 604/174 |
| 4,808,163 A | 2/1989 | Laub ............................. 604/105 |
| 4,878,893 A | 11/1989 | Chin ............................... 604/21 |
| 4,904,238 A | 2/1990 | Williams ........................ 604/43 |
| 4,936,826 A | 6/1990 | Amarasinghe .................. 604/52 |

(Continued)

FOREIGN PATENT DOCUMENTS

| EP | 0 301 854 A2 | 2/1989 |
| WO | WO 01/019425 A1 | 3/2001 |

(Continued)

OTHER PUBLICATIONS

International Search Report and Written Opinion issued in International Application No. PCT/US2010/058036, dated May 30, 2011, 14 pgs.

*Primary Examiner* — Philip R. Wiest
(74) *Attorney, Agent, or Firm* — Brinks Hofer Gilson & Lione

(57) ABSTRACT

A catheter for use in the extracorporeal treatment of bodily fluids comprises a catheter body having a withdrawal port, an infusion port, and a plurality of lumens therein. The lumens comprise two or more withdrawal lumens that merge to form a single lumen proximal to withdrawal ports for transport of fluids withdrawn from a body vessel through the withdrawal port to an extracorporeal treatment unit, such as a dialyzer. The lumens also comprise an infusion lumen for infusion of treated fluids from the extracorporeal treatment unit through the infusion port into the vessel. The infusion lumen is disposed substantially at the center of the catheter body, while the withdrawal lumens extend longitudinally adjacent the infusion lumen along the catheter body length. A manifold may be provided at the proximal end of the catheter body to include the merger of the withdrawal lumens.

20 Claims, 7 Drawing Sheets

U.S. PATENT DOCUMENTS

| | | | | |
|---|---|---|---|---|
| 4,973,301 | A | 11/1990 | Nissenkorn | 604/8 |
| 4,995,865 | A | 2/1991 | Gahara et al. | 604/43 |
| 4,995,868 | A | 2/1991 | Brazier | 604/105 |
| 5,106,368 | A | 4/1992 | Uldall et al. | 604/43 |
| 5,156,597 | A | 10/1992 | Verreet et al. | 604/175 |
| 5,193,533 | A | 3/1993 | Body et al. | 128/207.14 |
| 5,221,256 | A | 6/1993 | Mahurkar | 604/43 |
| 5,250,034 | A | 10/1993 | Appling et al. | 604/164 |
| 5,275,610 | A | 1/1994 | Eberbach | 606/198 |
| 5,352,198 | A | 10/1994 | Goldenberg et al. | 604/95 |
| 5,360,397 | A | 11/1994 | Pinchuk | 604/27 |
| 5,364,344 | A | 11/1994 | Beattie et al. | 604/43 |
| 5,395,316 | A * | 3/1995 | Martin | 604/43 |
| 5,403,291 | A | 4/1995 | Abrahamson | 604/280 |
| 5,409,460 | A | 4/1995 | Krumme | 604/107 |
| 5,443,449 | A | 8/1995 | Buelna | 604/105 |
| 5,486,159 | A | 1/1996 | Mahurkar | 604/4 |
| 5,489,278 | A | 2/1996 | Abrahamson | 604/280 |
| 5,509,897 | A | 4/1996 | Twardowski et al. | 604/43 |
| 5,509,900 | A | 4/1996 | Kirkman | 604/104 |
| 5,514,112 | A | 5/1996 | Chu et al. | 604/267 |
| 5,518,498 | A | 5/1996 | Lindenberg et al. | 600/30 |
| 5,522,400 | A | 6/1996 | Williams | 128/772 |
| 5,549,245 | A | 8/1996 | Kish | 238/283 |
| 5,571,093 | A | 11/1996 | Cruz et al. | 604/270 |
| 5,681,280 | A | 10/1997 | Rusk et al. | 604/95 |
| 5,702,365 | A | 12/1997 | King | 604/105 |
| 5,713,853 | A | 2/1998 | Clark et al. | 604/53 |
| 5,749,826 | A | 5/1998 | Faulkner | 600/29 |
| 5,817,067 | A | 10/1998 | Tsukada | 604/256 |
| 5,857,464 | A | 1/1999 | Desai | 128/658 |
| 5,885,258 | A | 3/1999 | Sachdeva et al. | 604/281 |
| 5,888,196 | A | 3/1999 | Bonutti | 600/204 |
| 5,957,900 | A | 9/1999 | Ouchi | 604/264 |
| 6,001,079 | A | 12/1999 | Pourchez | 604/43 |
| 6,033,397 | A | 3/2000 | Laufer et al. | 606/27 |
| 6,052,612 | A | 4/2000 | Desai | 600/435 |
| 6,071,263 | A | 6/2000 | Kirkman | 604/104 |
| 6,177,049 | B1 | 1/2001 | Schnell et al. | 422/44 |
| 6,238,412 | B1 | 5/2001 | Dubrul et al. | 606/200 |
| 6,270,490 | B1 | 8/2001 | Hahnen | 604/509 |
| 6,283,940 | B1 | 9/2001 | Mulholland | 604/96.01 |
| 6,293,958 | B1 | 9/2001 | Berry et al. | 606/191 |
| 6,336,933 | B1 | 1/2002 | Parodi | 606/139 |
| 6,409,700 | B1 | 6/2002 | Siegel, Jr. et al. | 604/43 |
| 6,461,321 | B1 | 10/2002 | Quinn | 604/43 |
| 6,475,207 | B1 | 11/2002 | Maginot et al. | 604/508 |
| 6,482,169 | B1 | 11/2002 | Kuhle | 604/6.16 |
| 6,517,529 | B1 | 2/2003 | Quinn | 604/528 |
| 6,527,737 | B2 | 3/2003 | Kaneshige | 604/48 |
| 6,547,761 | B2 | 4/2003 | Liu | 604/104 |
| 6,558,349 | B1 | 5/2003 | Kirkman | 604/104 |
| 6,558,350 | B1 | 5/2003 | Hart et al. | 604/104 |
| 6,569,150 | B2 | 5/2003 | Teague et al. | 604/524 |
| 6,579,302 | B2 | 6/2003 | Duerig et al. | 606/198 |
| 6,758,836 | B2 | 7/2004 | Zawacki | 604/284 |
| 6,767,339 | B2 | 7/2004 | Reydel | 604/175 |
| 6,966,886 | B2 | 11/2005 | Appling | 604/6.16 |
| 7,001,354 | B2 | 2/2006 | Suzuki et al. | 604/6.11 |
| 2001/0011182 | A1 | 8/2001 | Dubrul et al. | 606/200 |
| 2001/0018576 | A1 | 8/2001 | Quinn | 604/264 |
| 2001/0041858 | A1 | 11/2001 | Ray et al. | 604/93.01 |
| 2002/0026156 | A1 | 2/2002 | Quinn | 604/264 |
| 2002/0072768 | A1 | 6/2002 | Ginn | 606/213 |
| 2002/0107506 | A1 | 8/2002 | McGuckin, Jr. et al. | 604/523 |
| 2002/0143292 | A1 | 10/2002 | Flinchbaugh | 604/107 |
| 2002/0177822 | A1 | 11/2002 | St. Cyr et al. | 604/264 |
| 2003/0032918 | A1 | 2/2003 | Quinn | 604/43 |
| 2003/0093029 | A1 * | 5/2003 | McGuckin et al. | 604/43 |
| 2003/0139763 | A1 | 7/2003 | Duerig et al. | 606/198 |
| 2004/0049157 | A1 | 3/2004 | Plishka et al. | 604/164.09 |
| 2004/0210180 | A1 * | 10/2004 | Altman | 604/4.01 |
| 2005/0033264 | A1 | 2/2005 | Redinger | 604/523 |
| 2005/0148929 | A1 | 7/2005 | Gingles | 604/95.04 |
| 2005/0177094 | A1 | 8/2005 | Igarashi et al. | 604/43 |
| 2005/0261663 | A1 | 11/2005 | Patterson et al. | 604/508 |
| 2006/0004325 | A1 | 1/2006 | Hamatake et al. | 604/43 |
| 2006/0253063 | A1 | 11/2006 | Schweikert | 604/30 |
| 2007/0016124 | A1 | 1/2007 | McGraw | 604/4.01 |
| 2009/0054824 | A1 | 2/2009 | Melsheimer et al. | 604/6.16 |
| 2009/0054825 | A1 | 2/2009 | Melsheimer et al. | 604/6.16 |

FOREIGN PATENT DOCUMENTS

| | | |
|---|---|---|
| WO | WO 01/32240 A1 | 5/2001 |
| WO | WO 02/064202 A3 | 8/2002 |
| WO | WO 03/066125 A | 8/2003 |
| WO | WO 2005/049125 A1 | 6/2005 |
| WO | WO 2006/002192 A2 | 1/2006 |

* cited by examiner

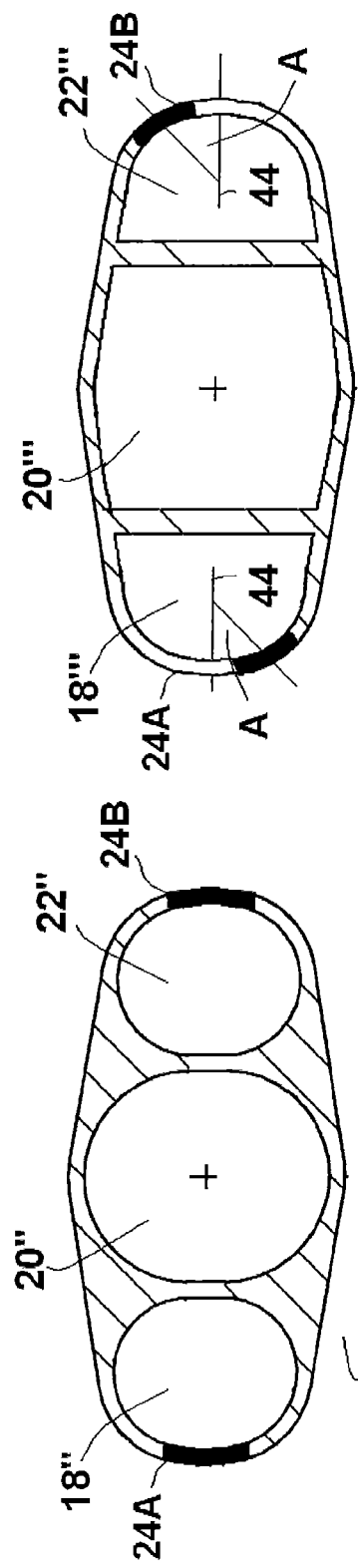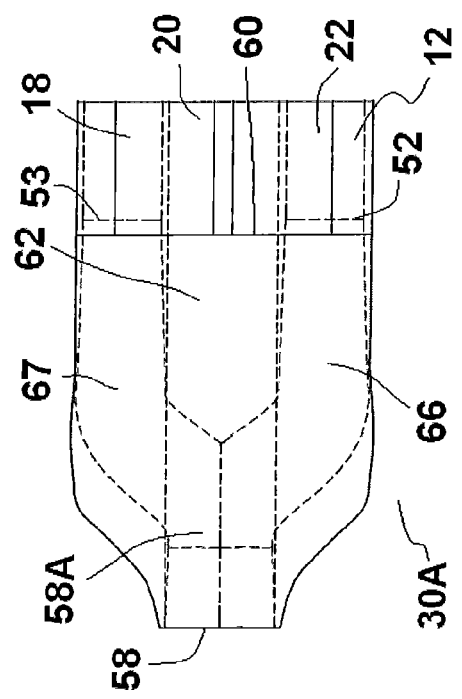

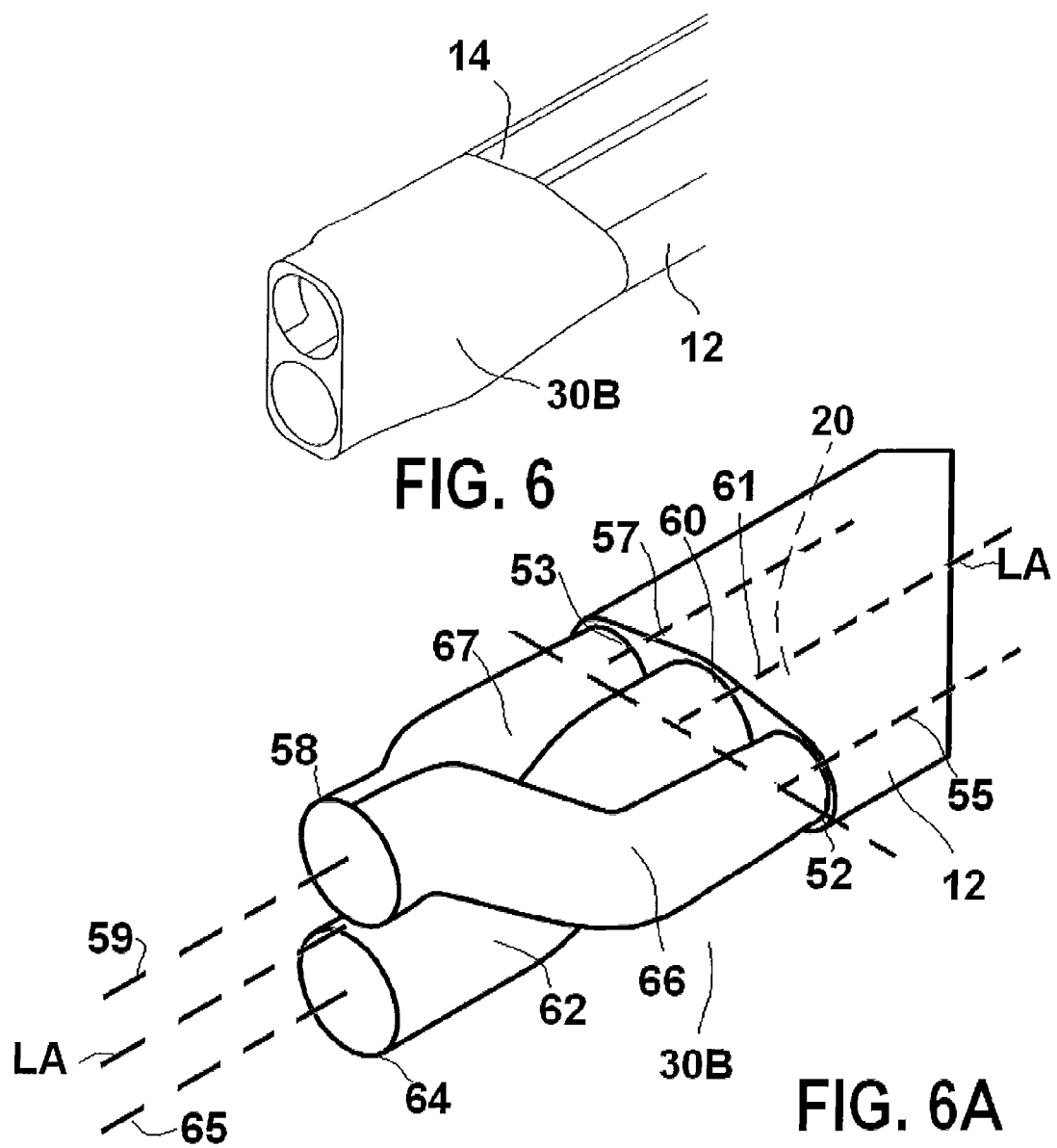

MULTI-LUMEN CATHETER

TECHNICAL FIELD

The present application relates generally to a medical device, such as a catheter, for use in transporting fluids. More particularly, the application relates to a multi-lumen catheter for transporting fluids from the patient's body for extracorporeal treatment, and returning the treated fluids to the body.

BACKGROUND INFORMATION

Dual lumen catheters are commonly used for transporting bodily fluids for treatment external of a patient's body, a process generally referred to in the medical field as "extracorporeal" treatment, and thereafter returning the treated fluid to the body. The fluid is withdrawn from the body through one of the lumens of the catheter, generally referred to as the withdrawal, or aspiration, lumen. The fluid is subjected to a treatment process, and thereafter returned to the body through the other lumen, generally referred to as the infusion, or return, lumen.

In many cases, the extracorporeal treatment is carried out as part of a hemodialysis procedure. During hemodialysis, blood is withdrawn from a blood vessel through the aspiration lumen and routed to a dialyzer for cleansing. The cleansed blood is then returned to the vessel through the infusion lumen. When such a catheter is used for hemodialysis, whether for acute (short-term, generally thirty days or less) or longer term hemodialysis, it is generally inserted into the body through the internal jugular vein, subclavian vein or femoral vein. In addition to hemodialysis, extracorporeal catheters can also be used for other procedures, such as pheresis and hemofiltration, in which a fluid is removed from the body for treatment and later returned to the body.

A variety of hemodialysis catheters are commercially available. Among the types of commercially available catheters are: 1) a dual lumen catheter having one lumen (e.g., the blood infusion lumen), that terminates distal to the other lumen (e.g., the blood aspiration lumen). Some catheters of this type are provided with a midline split between the withdrawal and infusion lumens, while others do not have such a split (e.g., the COOK® DDS catheter); 2) a catheter having a slitted valve in the distal tip that acts as a pressure valve opening. This valve opens inwardly for blood aspiration, outwardly for blood infusion, and remains closed when not in use (e.g., the Groshong catheter); 3) a cuffed central venous silicone catheter that is tunneled underneath the skin to reduce infection (e.g., Broviac, Leonard and Hickman catheters); 4) a dual lumen catheter having a tapered tip and two adjacent holes communicating with one lumen just proximal to the tip to assist with outflow, and two adjacent holes communicating with the other lumen (180 degrees removed) just proximal to the first set of holes to assist with inflow (e.g., the Mahurkar catheter); and 5) a dual lumen catheter having a diverting structure consisting of a shoulder that has a straight up distal face and a sloped proximal face to reduce access recirculation and raise pressure in the vicinity of the inlet aperture (U.S. Pat. No. 6,409,700).

One problem with existing multi-lumen catheters is that such catheters can experience decreased flow rates over time. Decreased flow rates may be caused by, among other things, blockage of the aspiration and/or infusion ports in the catheter. Various factors can cause a port to become blocked. One common cause of port blockage is the inadvertent positioning of one or more ports of the catheter against the vessel wall. This positioning hinders the free flow of fluid through the obstructed port, and in some cases, prevents fluid flow altogether. Another common cause of port blockage is the formation of fibrin sheaths along the ports. Fibrin sheaths may be formed, e.g., in response to the vessel wall washing effect or clotting.

Decreased, or restricted, flow is clearly undesirable in a multi-lumen catheter for use in extracorporeal treatment of a fluid, such as a hemodialysis catheter. In order for the extracorporeal fluid treatment to be effective, fluid flow through the catheter must not be restricted in any appreciable way. Thus, it is important to position existing catheters in a manner such that fluid flow is not restricted. Additionally, it is important to insure that all ports are unobstructed.

As indicated above, various attempts have been made in the art to reduce port blockage. Some catheters are provided with side ports at various locations on the catheter, which generally provide some reduction in port blockage, however such ports themselves are subject to blockage when placed against the vessel wall, or as a result of fibrin formation on the port. Other attempts have been made to reduce port blockage by providing the staggered side-by-side dual lumen design described above. Here, the respective aspiration and infusion tubes can be different lengths so that the ports aspirate and infuse the bodily fluid at different axial locations of the catheter, which can also reduce recirculation. While these, and other, arrangements may avoid some problems involved in maintaining adequate flow through the lumens, such catheters can still be subject to suboptimal flow. Some catheters, such as the Mahurkar catheter described above, must be rotated or repositioned if inflow is blocked because the catheter is up against the vein wall. Although each of these techniques may be at least partially effective in reducing some types of blockage, reduced flow rate continues to be a problem in the art.

It is desired to provide a multi-lumen catheter assembly for use in the extracorporeal treatment of bodily fluids, wherein the multi-lumen catheter assembly is structured in a manner to minimize port blockage, and to provide for optimal fluid flow through the lumens of the catheter.

SUMMARY

The shortcomings of the prior art are addressed by the various embodiments of a multi-lumen catheter described herein for use in the extracorporeal treatment of bodily fluids. In one embodiment, the catheter includes a catheter body having a length disposed about a longitudinal axis. The catheter body has a plurality of withdrawal ports and at least one infusion port disposed along the catheter body length. An infusion lumen in fluid communication with the at least one infusion port is disposed substantially at the center of the catheter body about the longitudinal axis, extending longitudinally along the catheter body length for transport of treated fluids from the extracorporeal treatment unit into the body vessel through the infusion port. Two or more withdrawal lumens in fluid communication with at least one of said withdrawal ports are included in the catheter body. A first withdrawal lumen extends longitudinally adjacent the infusion lumen along the catheter body length, and a second withdrawal lumen extends longitudinally adjacent the infusion lumen along the catheter body length. The withdrawal lumens can be disposed opposite, preferably diametrically opposed, to one another at opposite sides of said infusion lumen. The catheter body can be configured such that the first and second withdrawal lumens merge along a portion of the catheter body proximal to the withdrawal ports for transport of bodily fluids withdrawn from a body vessel to the extracorporeal treatment unit. The first and second withdrawal lumens can have a cross-sectional area sized to permit sufficient fluid flow rate for continuous extracorporeal treatment without stoppage.

In another embodiment, the catheter includes a catheter body having a length disposed about a longitudinal axis. The catheter body has a plurality of withdrawal ports and at least one infusion port disposed along the catheter body length. An infusion lumen in fluid communication with the at least one infusion port is disposed substantially at the center of the catheter body about the longitudinal axis, extending longitudinally along the catheter body length for transport of treated fluids from the extracorporeal treatment unit into the body vessel through the infusion port. First and second withdrawal lumens in fluid communication with at least one of said withdrawal ports are included in the catheter body. The first withdrawal lumen extends longitudinally adjacent the infusion lumen along the catheter body length, and the second withdrawal lumen extends longitudinally adjacent the infusion lumen along the catheter body length. The withdrawal lumens can be disposed opposite to one another at opposite sides of said infusion lumen. The catheter body has a manifold coupled to the proximal end of the catheter body configured for the merger of the first and second withdrawal lumens. The connection between the catheter body and the extension tubes can either be via separate conduits, or can be via a molded body containing the conduits.

In one aspect, the manifold preferably includes an outlet port, an inlet port coupled to each of the withdrawal lumens, and a withdrawal conduit coupled to each inlet port. Each of the withdrawal conduits can be angled vertically and horizontally toward the center such that the withdrawal conduits intersect to form a single conduit leading to the outlet port. The manifold can also include an inlet port, an outlet port coupled to the infusion lumen, and an infusion conduit coupled between the inlet and outlet ports, which can be angled vertically away from the withdrawal conduit. The inlet port coupled to the infusion conduit and the outlet port coupled to the single conduit of the withdrawal conduit can be in vertical alignment. Further, the outlet port coupled to the infusion lumen and the inlet ports coupled to the withdrawal lumens can be in horizontal alignment and disposed at opposite sides of the outlet port coupled to the infusion lumen.

In yet another embodiment, the invention comprises a method for treating a body fluid with one of the various embodiments of the catheter described herein. For example, the first and second withdrawal lumens can merge along a portion of the catheter body proximal to the withdrawal ports. To this end, a distal end of a catheter can be inserted into the vessel. Body fluid to be treated can be withdrawn from the vessel through the withdrawal ports. The withdrawn fluid is transported to a treatment instrument through the withdrawal lumens. Following treatment in the treatment instrument, the fluid is transported from the treatment instrument through the infusion lumen, and infused into the body vessel through the infusion port.

BRIEF DESCRIPTION OF THE DRAWINGS

FIGS. 4B-4C are transverse sectional views of alternative embodiments of a catheter assembly, depicting alternative-shaped lumens.

FIG. 5B is a top view of the manifold of FIG. 5, depicting the merger of lumens of the manifold.

FIG. 6 is a perspective view of an alternative manifold provided with a catheter assembly.

FIG. 6A is a perspective view of the manifold of FIG. 6, depicting the lumens of the manifold.

DETAILED DESCRIPTION OF THE DRAWINGS AND THE PRESENTLY PREFERRED EMBODIMENTS

Figure 1:
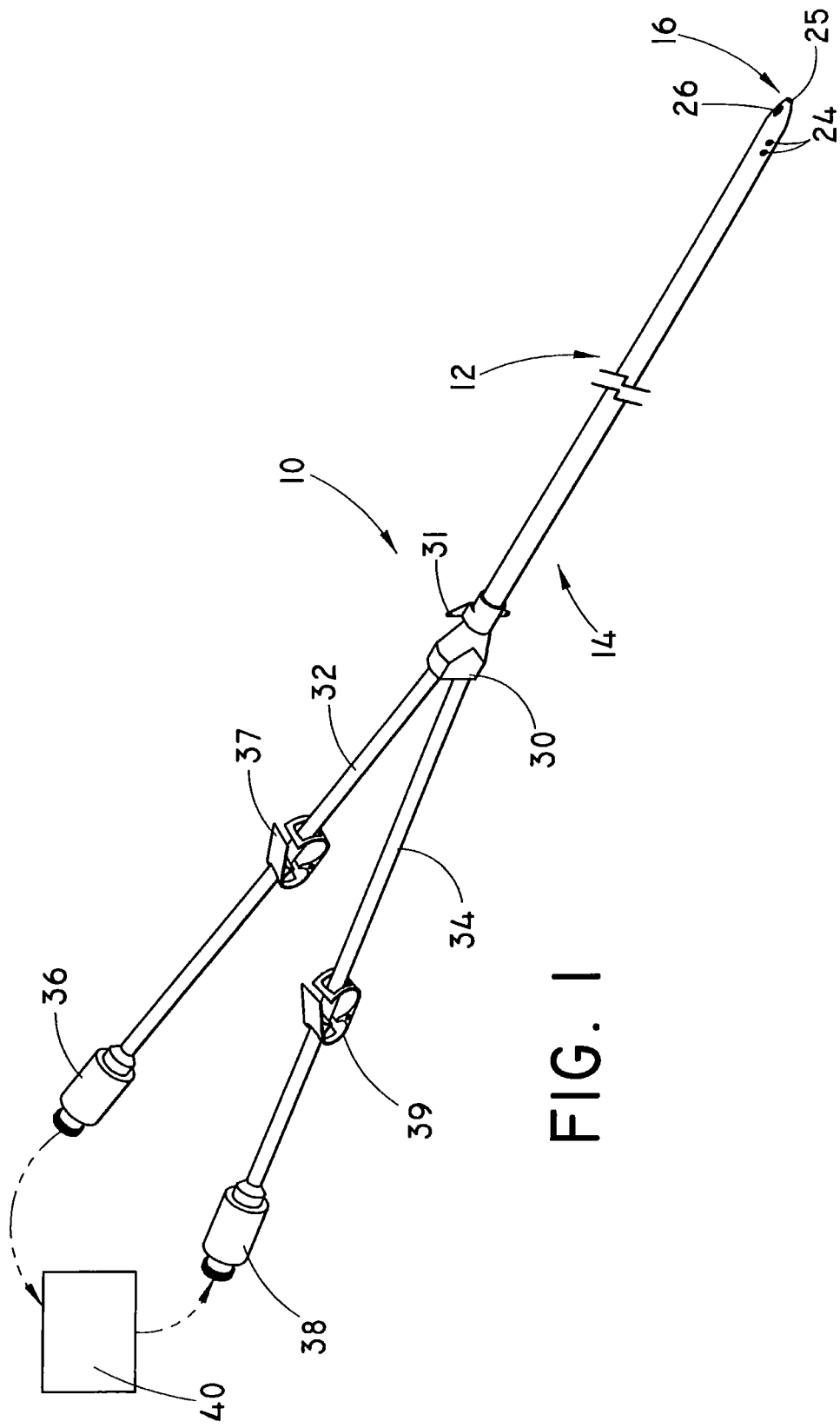
FIG. 1 is a perspective view of one embodiment of a catheter assembly.

For purposes of promoting an understanding of the present invention, reference will now be made to the embodiments illustrated in the drawings, and specific language will be used to describe the same. It is nevertheless to be understood that no limitation of the scope of the invention is thereby intended, the scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein.

The present invention is directed to a multi-lumen catheter for use in the transport of bodily fluids for treatment external of the body, referred to in the medical arts as "extracorporeal" treatment. The bodily fluids are transported from the body through one or more withdrawal lumens in the catheter, and are thereafter transported to an instrument for extracorporeal treatment. The treated fluids are then returned, or infused, to the body through an infusion lumen in the catheter.

In the following discussion, the terms "proximal" and "distal" will be used to describe the axial ends of the catheter, as well as the axial ends of various component features. The "proximal" end is used in conventional manner to refer to the end of the catheter (or component) that is closest to the operator during use of the assembly. The "distal" end is used in conventional manner to refer to the end of the catheter (or component) that is initially inserted into the patient, or that is closest to the patient.

Those skilled in the art will appreciate that the catheter described herein is suitable for multiple uses involving inflow and outflow of bodily fluids. However, the invention will be primarily described hereinafter with reference to one of its intended uses, namely as a hemodialysis catheter for use in the extracorporeal treatment of blood. The hemodialysis catheter enables blood inflow without disturbance, and blood return without hemolysis. In addition to hemodialysis, the catheter can be used for other extracorporeal fluid treatments in which a body fluid is withdrawn from the body, subjected to a treatment process, and thereafter returned to the body. Pheresis and hemofiltration are non-limiting examples of such additional procedures. The dimensions and configurations of various components described herein are particular suitable for use in extracorporeal treatment, although the dimensions can vary as needed depending on the type of use in other applications.

FIG. 1 is a perspective view of a catheter assembly 10 according to one embodiment of the present invention. Catheter assembly 10 includes a catheter body 12. Catheter body 12 comprises an elongated tubular member formed of a conventional polymer commonly used for such purposes in medical catheters, such as radiopaque polyurethane. Other conventional materials used for such purposes in the medical device art may be substituted. Non-limiting examples of such materials include silicone, polyurethane and PTFE. Typically, catheter body 12 will be formed by a conventional extrusion process. Catheter body 12 has a proximal end 14, a distal end 16, and includes a plurality of lumens 18, 20, 22 extending at least partially therethrough (FIGS. 3 and 4).

Figure 2:
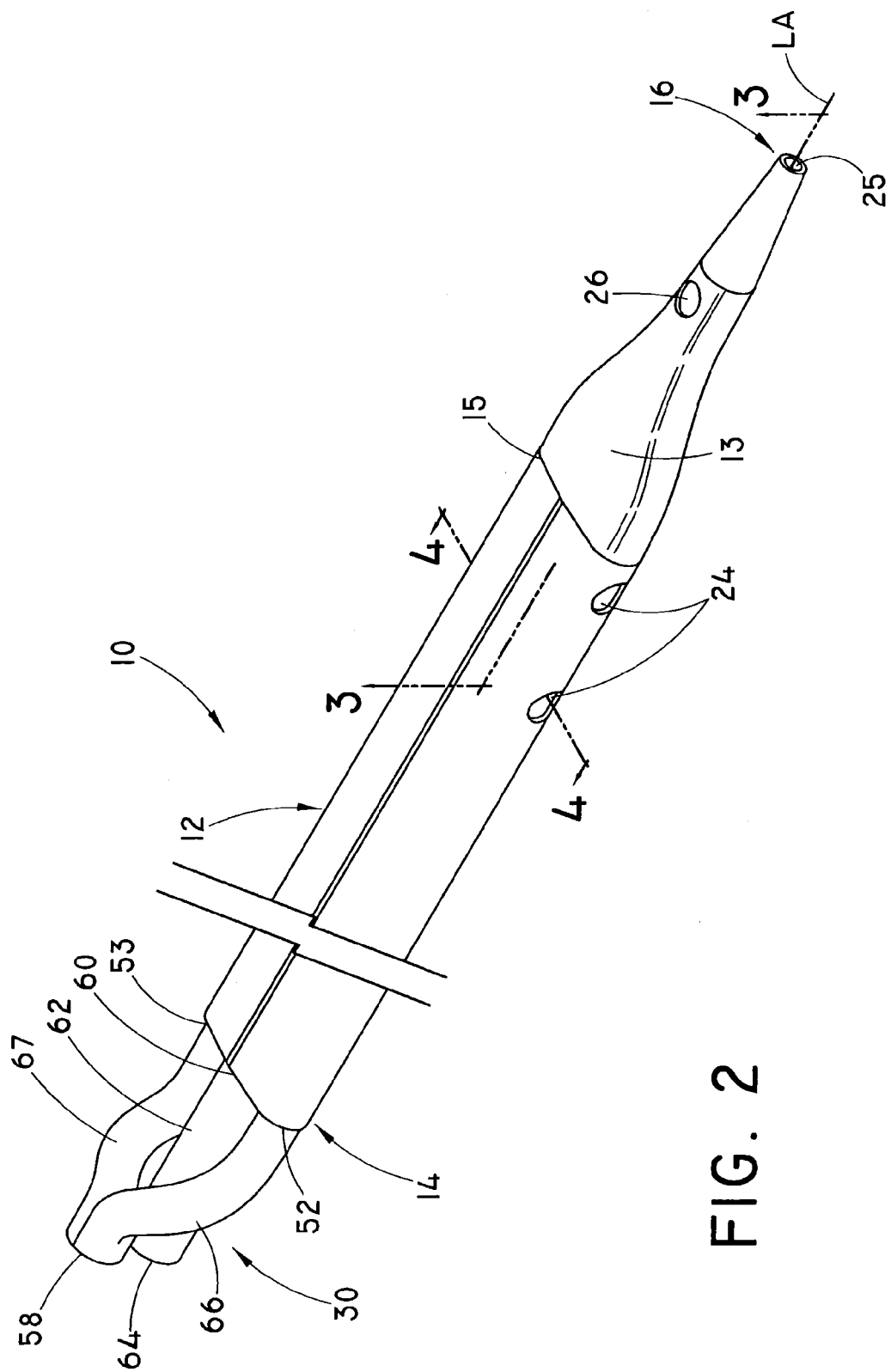
FIG. 2 is an enlarged perspective view of the distal end of the catheter assembly of FIG. 1.

FIG. 2 is an enlarged perspective view of the catheter body 12 of the catheter assembly 10 of FIG. 1. FIG. 3 is a longitudinal sectional view of catheter assembly 10 taken along line 3-3 of FIG. 2. FIG. 4 is a transverse sectional view of catheter assembly 10, taken along line 4-4 of FIG. 2. FIGS. 3 and 4 illustrate lumens 18, 20, 22 that extend longitudinally through at least the major portion of the length of catheter body 12. In the preferred arrangement depicted in the figures, two or more lumens 18, 22 are the fluid aspiration, or withdrawal, lumens, and lumen 20 is the fluid infusion, or return, lumen. Those skilled in the art will appreciate that with minor modification, this arrangement of lumens can be reversed. Septums 21, 23 are provided internally of catheter body 12 to separate lumens 18 and 22 from lumen 20. In the embodiment shown, aspiration lumens 18, 22 extend from aspiration ports 24 to the proximal end of catheter body 12. In preferred embodiments, infusion lumen 20 is disposed substantially at the center of catheter body about the longitudinal axis of the catheter body. The withdrawal lumens 18, 22 can be disposed on the opposite sides of infusion lumen 20, preferably diametrically opposite to one another. Aspiration ports 24 are sized depending on the catheter body size and the required flow rates, e.g., the ports can have an outer diameter of about 0.070 inches. The most distal withdrawal port is longitudinally spaced from distal end 16 by a distance sufficient to inhibit recirculation, e.g., about 40-50 mm, or optionally can be spaced from the most proximal infusion port by at least 30 mm.

Figure 3:
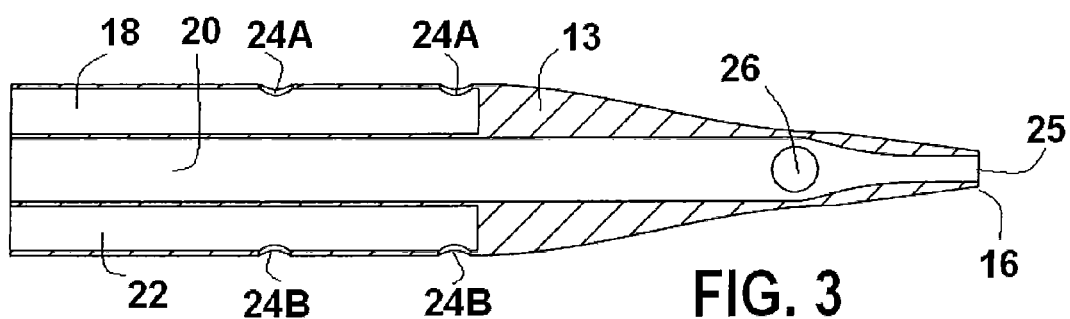
FIG. 3 is a longitudinal sectional view of the catheter assembly taken along line 3-3 of FIG. 2.
Figure 4:
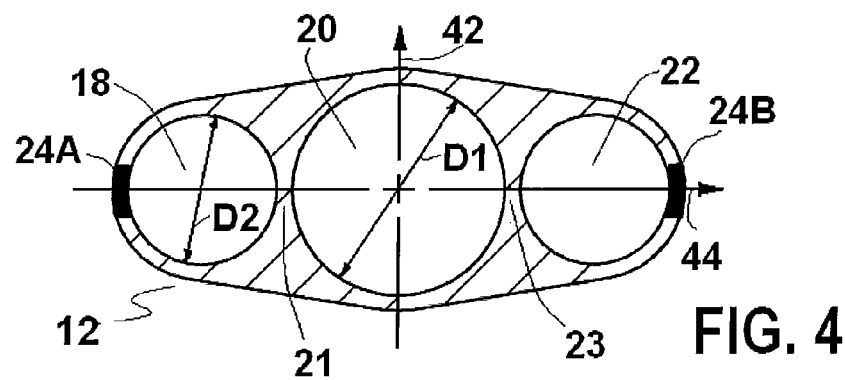
FIG. 4 is a transverse sectional view of the catheter assembly taken along line 4-4 of FIG. 2.

As shown in FIG. 3, aspirations ports 24 can be further subdivided into aspiration ports 24A in fluid communication with aspiration lumen 18, and aspiration ports 24B in fluid communication with aspiration lumen 22. Although two aspiration ports per aspiration lumen are shown, it is to be understood that one or any number of ports can be included. Aspiration ports 24A and 24B are shown in the figures to be aligned along the same plane, yet ports 24A, 24B may be positioned in a staggered fashion, or axially offset, at opposite sides of the catheter body such that ports 24A are longitudinally spaced, e.g., about 5-10 mm, from ports 24B. Further, ports 24A and 24B are shown in FIG. 4 to be facing 180 degrees opposite to one another along the same line, yet the ports can face in different directions so as to not be to facing 180 degrees opposite, such as, e.g., angle A of up to about 45 degrees from axis 44, as shown in FIG. 4C. Beading or other "filler" material can be provided in the lumen space between aspiration port and the closed distal end of lumens. Adding filler material to the otherwise unused, or "dead", space distal of the aspiration port increases the efficiency of the flow, and more importantly eliminates the dead space that can allow pooling of blood and formation of clots. If desired, additional aspiration ports can be formed along the length of catheter body 12 to increase fluid flow into the aspiration lumens 18, 22. Aspiration ports 24 may also be defined by flaps as described in U.S. Patent App. Publ. No. 2009/0054825A1 to Melsheimer et al., which is incorporated herein by reference in its entirety, however this is not necessarily required, and such additional ports may have other configurations suitable for aspiration of a fluid.

With reference to FIGS. 2 and 3, adjacent distal end 16 of catheter body 12 is a tapered catheter body segment 13 that has a proximal end 15 which is configured to match the general cross-sectional shape of catheter body 12. From proximal end 15, catheter body segment 13 is further configured to transition sufficiently to a smaller cross-sectional area in a more distal direction to distal end 16 to facilitate insertion into the vessel. The distance from proximal 15 to distal end 16 can vary depending on the application, e.g., the distance can be about 40-50 mm. Devices for forming tip configurations are well known in the medical arts, and those skilled in the art can readily adapt such a device to form catheter body segment 13 and tapered distal end 16. As shown in FIG. 2, catheter body segment 13 transitions from an elliptical cross-sectional area at the proximal end 15 to a more circular cross-sectional area at an intermediate portion between proximal end 15 of catheter body segment 13 and distal end 16 of catheter body 12.

Fluid infusion lumen 20 typically extends from an infusion port 25 at distal end 16 to proximal end 14 of catheter body 12. In the preferred embodiment shown, infusion port 25 comprises an opening at the distal end of catheter body 12 in communication with infusion lumen 20. If desired, one or more side infusion ports 26 may be provided along the length of catheter body 12 that also communicate with infusion lumen 20. The distance and spacing of additional ports will depend on the catheter body size and the desired flow rate. For example, the most distal side infusion port 26 can be spaced from the catheter distal end 16 by about 9 mm to about 13.5 mm, and additional ones spaced about 2 mm to about 6 mm apart from one another. Side port 26 provides extra cross-sectional area for infusion of treated blood into the vessel in addition to infusion port 25. The total combined cross-sectional areas of infusion port 25 and side port(s) 26 is at least as great as the cross-sectional area of the infusion lumen. For example, infusion port 25 can have an outer diameter of about 0.035 inches and side port 26 can have an outer diameter of about 0.120 inches. As a result, the infusion flow rate will not be reduced due to the reduction in diameter at the tapered distal tip, and fluid will not be backed-up in the infusion lumen. All of the various ports described herein may be formed in conventional fashion, such as by punching or skiving the ports through catheter body 12.

Preferably, aspiration ports 24A, 24B are positioned proximal to infusion port 25 and side port 26 along the length of catheter body 12. This arrangement is preferred, but not crucial to the invention. Positioning the aspiration port(s) proximal to the infusion port and side port(s) enhances the efficiency of the extracorporeal procedure, by assuring that the majority of the blood that is aspirated through the aspiration port(s) is not the same blood that has previously been cleansed and returned to the vessel through the infusion port and/or side port.

With reference to FIGS. 1 and 2, in the preferred embodiment shown, catheter assembly 10 includes a fitting, such as a manifold 30. Manifold 30 may be provided with conventional suture wings 31 if desired. Extension tubes 32, 34 extend in the proximal direction from manifold 30. Extension tubes 32, 34 comprise generally flexible polymers commonly used for such purposes in the medical device art, such as polyurethane, PVC and silicone. Catheter body 12 is received in manifold 30 in conventional fashion, such as by insert molding catheter body proximal end 14 in a suitably-sized channel in manifold 30. Extension tube 32 communicates with fluid aspiration lumens 18, 22 in catheter body 12 for receiving fluid withdrawn from a body vessel in the patient and transporting fluid to a treatment instrument 40, such as a dialyzer. A luer lock or other suitable connector 36 is fitted onto the proximal end of extension tube 32 in conventional fashion. During use of catheter assembly 10, connector 36 is engaged in mating relationship with a connector associated with an ingress opening of dialyzer 40 for establishing a flow path of blood to the dialyzer.

Extension tube 34 communicates with blood infusion lumen 20 in catheter body 12. A luer lock or other suitable connector 38 is fitted onto the proximal end of extension tube 34. Connector 38 is engaged in mating relationship with a connector associated with an egress opening of dialyzer 40 for receiving treated blood from the dialyzer, where the treated blood is returned to infusion lumen 20 for reentry into the body, preferably through infusion port 25 and side port 26. Dialyzer 40 and its ingress and egress openings are shown schematically in FIG. 1. Conventional clamps 37, 39 may be provided for closing off the flow of blood between the dialyzer and the catheter body when not the dialyzer is not in use.

The lumens 18, 20, 22 can be a variety of shapes or a combination of shapes so long as the lumens are sized to balance infusion and aspiration fluid flow rates, while maximizing the ratio of lumen space to catheter body material. As shown in FIG. 4, the lumens 18, 20, 22 can be circular and sized to permit sufficient fluid flow rates between aspiration lumens 18, 22 and infusion lumen 20. Preferably, each of the aspiration lumens 18, 22 is sized to permit sufficient fluid flow rate for continuous extracorporeal treatment without stoppage, in the case where catheters can experience decreased flow rates over time due to blockage of the aspiration and/or infusion ports in the catheter. The desired flow rate will be dependent on the ratings of the dialyzer, which is typically 300 mL/mm but can be up to 500 mL/mm if the catheter body and lumens are suitably sized. Infusion lumen 20 can be sized having a diameter D1, and each of aspiration lumens 18, 22 can be sized have a diameter D2. Diameter D2 can be 50-100% (D1) and preferably 80-90% (D1), and accordingly, the cross-sectional area of each of the withdrawal lumens, regardless of its shape, can be 50-100%, preferably 65-75%, the cross-sectional area of the infusion lumen.

In some embodiments, the diameter D1 of infusion lumen 20, in addition to a predetermined material thickness for forming the lumen, forms the distance of catheter body 12 along a first direction 42. Moreover, the diameter D1 of infusion lumen 20 and the diameter D2 (FIG. 4), or distance of crescent-shaped lumen radially outward (FIG. 4A), of withdrawal lumens 18, 22, in addition to a predetermined material thickness of both septums 21, 23 and outside walls for forming the lumens, forms the distance of catheter body 12 along a second direction 44, perpendicular to the first direction. Having the withdrawal lumens 18, 22 disposed on the opposite sides of infusion lumen 20, preferably diametrically opposite and in alignment along the second direction, can permit the aspiration ports 24A and 24B to be disposed on opposite sides of said catheter body. One advantage of this configuration is that when one withdrawal port at one side is inadvertently positioned against the vessel wall, which typically inhibits flow therethrough, another withdrawal port at the opposite side is available and sized for continuous extracorporeal treatment. This can shorten the overall duration of treatment by avoiding stoppage of treatment to reposition and/or flush the catheter, or even avoiding the removal and replacement of the catheter.

Figure 3A:
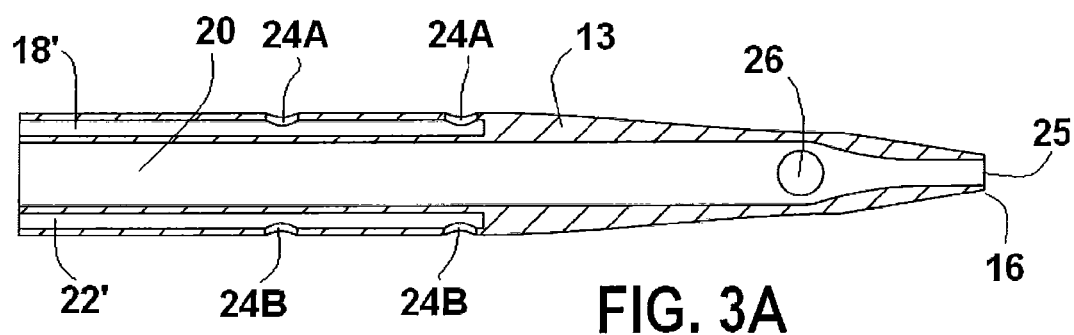
FIG. 3A is a longitudinal sectional view of the catheter assembly similar to FIG. 3, depicting an alternative embodiment of a catheter assembly.
Figure 4A:
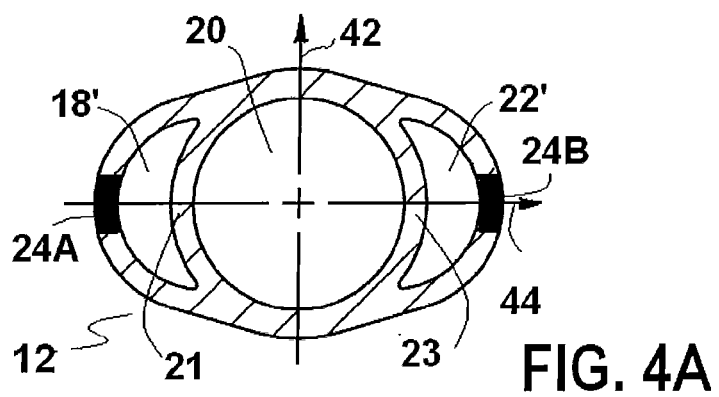
FIG. 4A is a transverse sectional view of the catheter assembly similar to FIG. 4, depicting an alternative embodiment of a catheter assembly.

The cross-sectional shape of catheter body 12 can be a variety of shapes, such as oblong or elliptical (FIGS. 4, 4B, and 4C) to more circular (FIG. 4A). The desired shape of the catheter body will be dependent of the size and cross-sectional shape of the body vessel. FIG. 3A is a longitudinal sectional view similar to FIG. 3 of an alternative catheter assembly, while FIG. 4A is a transverse sectional view similar to FIG. 4 of the alternative catheter assembly of FIG. 3A, which is identical to catheter assembly 10 in all aspects except the cross-sectional shape of the aspiration lumens and catheter body. FIGS. 3A and 4A depict a more circular cross-sectional shape of the catheter body, where the cross-sectional shape of aspiration lumens 18', 22' is a crescent. As shown in FIG. 4A, the shape of aspiration lumens 18', 22' can decrease the width of the catheter body in the second direction as compared to the catheter body depicted in FIG. 4. FIGS. 4B-4C depict transverse sectional view of other embodiments of the catheter body. FIG. 4B illustrates the cross-sectional shape of the lumens 18", 20", 22" being elliptical. FIG. 4C illustrates the cross-sectional shape of aspiration lumens 18''', 22''' being D-shaped and infusion lumen 20''' being generally rectangular, where the top and bottom edges can be arcuate to match the curvature of the catheter body. FIG. 4C also illustrates the ports 24A, 24B can be place at angle A from axis 44, e.g., about 30 degrees from axis though it can be any desired angle suitable to inhibit total blockage of flow therethrough. Those skilled in the art will appreciate that the cross-sectional shape of the aspiration lumens and the infusion lumen can be any shape described herein or any combination thereof, and even the aspiration lumens can have a different shape.

Manifold 30 provides a sufficient number of ports for fluid communication between the multi-lumen catheter and the extension tubes. As depicted in FIG. 2, manifold 30 includes inlet aspiration ports 52, 53 for coupling with the proximal end of aspiration lumens 18, 22 of the catheter body. Attached to inlet ports 52, 53 are conduits 66, 67 that can be inclined in the vertical direction and to the center to intersect with one another such that the respective lumens of conduits 66, 67 are joined in fluid communication to form a single outlet aspiration port 58. Manifold 30 also includes an outlet infusion port 60 for coupling with the proximal end of infusion lumen 20 of the catheter body. Attached to outlet port 60 is a conduit 62 leading to an inlet infusion port 64. The catheter body proximal end 14 may be insert molding with suitably-sized conduits in manifold 30 in order to couple inlet ports 52, 53 with the lumens 18, 22, as well as outlet port 60 with lumen 20, respectively. Outlet port 58 and inlet port 64 are each adapted for coupling with the distal end of extension tubes 32, 34, respectively, in a conventional fashion.

Figure 5:
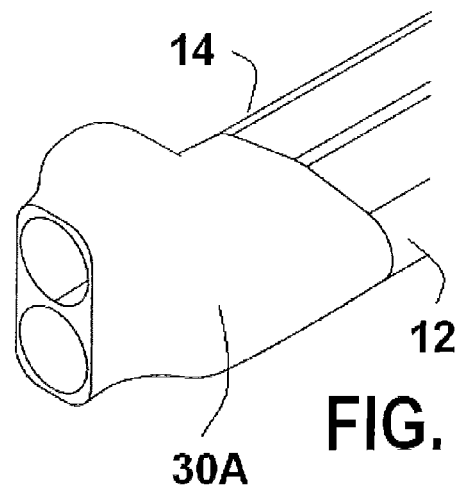
FIG. 5 is a perspective view of a manifold provided with a catheter assembly.

FIG. 2 depicts manifold 30 comprising of independent conduits that can be arranged as described herein. Alternatively, manifold 30 can also be molded, as described herein, such as via a conventional injection molding process, to the general shape illustrated in one of the figures to define the conduits, instead of comprising independent conduits. Molding may be particularly appropriate for the manifold that includes the merging of lumens and the inclined conduits, as it provides a very convenient way of forming the requisite manifold structure. The molded segment may then be attached by conventional means, such as adhesion, bonding, etc., to adjoining body segments, such as the manifold to the catheter body, which may or may not be molded. Further, typically the manifold can be insert molded, simultaneously with the catheter body, but other methods can be used as appreciated by the skilled artisan. In order to provide a secure attachment between the segments, it is preferred that the respective segments be formed from the same, or a similar, composition. FIG. 5 is a perspective view of one embodiment of a molded manifold 30A coupled to distal end 14 of catheter body 12. FIG. 6 is a perspective view another embodiment of a molded manifold 30B coupled to distal end 14 of catheter body 12. These figures depict the distal end of the molded manifold having the same shape as the proximal end of the catheter body.

Figure 5A:
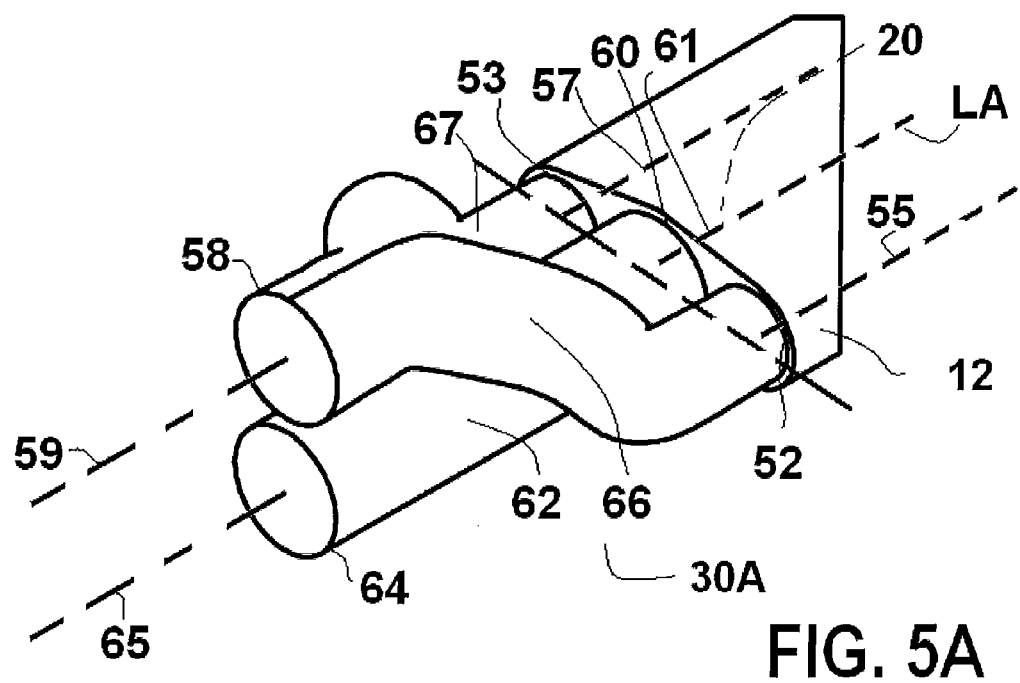
FIG. 5A is a perspective view of the manifold of FIG. 5, depicting the lumens of the manifold.

FIGS. 5A and 6A are perspective views of different embodiments of manifold 30A and 30B, respectively, illustrating the different arrangement of the conduits.

For example, FIG. 5A depicts the longitudinal axis 65 of inlet port 64 of manifold 30A in axial alignment with the longitudinal axis 61 of outlet port 60, each in alignment with the longitudinal axis LA of infusion lumen 20 of catheter body 12. The configuration would allow the bottom surface of the manifold and the catheter to be aligned such that the bottom surface could lie flat on the skin of the patient. Outlet port 58 is in vertical alignment with inlet port 64 such that the longitudinal axis 59 of outlet port 58 is vertically spaced from the longitudinal axis 65 of inlet port 64 along the first direction. As depicted, inlet ports 52, 53 are in horizontal alignment with outlet port 60 such that the longitudinal axes 55, 57 of inlet ports 52, 53 are horizontally spaced from the longitudinal axis LA along the second direction.

FIG. 5B depicts a top view of manifold 30A in FIG. 5. Conduits 62, 66, 67 are shown in dashed lines and, in particular, conduits 67, 66 are shown merging to form a single conduit 58A leading to outlet port 58. Inlet ports 52, 53 can also be inserted into the respective lumens 18, 22 for a fluid-tight seal, as shown.

Alternatively, FIG. 6A depicts the longitudinal axes of inlet port 64 or outlet port 58 of the manifold not in alignment with the longitudinal axis LA of infusion lumen 20 of catheter body 12. To this end, inlet port 64 and outlet port 58 of manifold 30B are in vertical alignment with one another such that the longitudinal axes 59, 65 of each are vertically spaced, preferably equidistant, from the longitudinal axis LA along the first direction. As depicted, ports 52, 53 are in horizontal alignment with port 60 such that the longitudinal axes of ports 52, 53 are horizontally spaced from the longitudinal axis LA, preferably equidistant along the second direction. As shown, conduits 66, 67 are each inclined in the vertical direction and to the center, and conduit 62 is inclined in the vertical direction in an opposite direction as conduits 66, 67.

The features described above can be supplemented with other known materials and techniques to improve various properties of the catheter assembly. For example, one or more radiopaque markers can be added along the length of the catheter body, or a radiopaque material may be added to the matrix of all or a part of the catheter body to improve visualization of the catheter in accordance with well-known techniques. Similarly, the catheter body may include a hydrophilic coating along all or a part of the length of the catheter to facilitate entry into the vessel. As yet another alternative, the catheter body can be coated or impregnated with various medicaments along all or a part of the length of the catheter body. Non-limiting examples of such medicaments include antiproliferatives, anticoagulants, thrombolytics, fibrinolytics, and antimicrobials.

Although the figures provided herein illustrate single body catheters such as the COOK DDS catheters, available from Cook Critical Care, of Bloomington, Ind., those skilled in the art will recognize that the invention is equally applicable with only minor modification to use with other conventional catheters, such as split-body catheters.

Insertion of the catheter into the vessel can be made over a wire guide, e.g., via the well-known Seldinger percutaneous entry technique. A distal end of one of the described catheters can be inserted into the vessel. Body fluid to be treated can be withdrawn from the vessel through the withdrawal ports. The withdrawn fluid is transported to a treatment instrument through the withdrawal lumens. Following treatment in the treatment instrument, the fluid is transported from the treatment instrument through the infusion lumen, and infused into the body vessel through the infusion port. Transport of bodily fluid to the dialyzer and return of the treated fluid to the body vessel follows a path as known in the art, and need not be further discussed for an understanding of the present invention.

It is therefore intended that the foregoing detailed description be regarded as illustrative rather than limiting, and that it be understood that it is the following claims, including all equivalents, that are intended to define the spirit and scope of this invention.

The invention claimed is:

1. A multi-lumen catheter for use in the extracorporeal treatment of bodily fluids with an extracorporeal treatment unit, comprising:
    a catheter body having a length disposed about a longitudinal axis, said catheter body having a plurality of withdrawal ports and at least one infusion port disposed along said catheter body length,
    said catheter body having first and second withdrawal lumens, each withdrawal lumen in fluid communication with at least one of said withdrawal ports, said catheter body configured such that the first and second withdrawal lumens merge along a portion of said catheter body proximal to said withdrawal ports for transport of bodily fluids withdrawn from a body vessel to said extracorporeal treatment unit, and an infusion lumen in fluid communication with the at least one infusion port, said infusion lumen extending longitudinally along said catheter body length for transport of treated fluids from said extracorporeal treatment unit into the body vessel through said at least one infusion port,
    wherein the infusion lumen is disposed substantially at the center of said catheter body about said longitudinal axis, said first withdrawal lumen extending longitudinally adjacent said infusion lumen along said catheter body length, and said second withdrawal lumen extending longitudinally adjacent said infusion lumen along said catheter body length, and
    wherein said catheter body comprises a manifold disposed at a proximal end of said catheter body and configured for merger of the first and second withdrawal lumens, and wherein the manifold comprises an infusion conduit coupled to the infusion lumen and in axial alignment with said longitudinal axis, and a withdrawal conduit coupled to each of the first and second withdrawal lumens and angled vertically away from said longitudinal axis.

2. The catheter of claim 1, wherein said withdrawal lumens are disposed at opposite sides of said infusion lumen.

3. The catheter of claim 2, wherein said withdrawal lumens are disposed diametrically opposed to another at opposite sides of said infusion lumen such that respective axes of the withdrawal lumens and the infusion lumen are in alignment.

4. The catheter of claim 2, wherein each withdrawal lumen has a cross-sectional area that is between about 65% and about 75% of a cross-sectional area of the infusion lumen.

5. The catheter of claim 2, wherein said withdrawal ports are disposed proximal to the at least one infusion port along said length, said withdrawal ports are disposed along said catheter body length such that the withdrawal ports of the first withdrawal lumen and the withdrawal ports of the second withdrawal lumen are at opposite sides of said catheter body.

6. The catheter of claim 1, wherein at least a portion of a distal end of said catheter body tapers from a larger cross-sectional area to a smaller cross-sectional area distal tip portion.

7. The catheter of claim 6, wherein the at least one infusion port comprises an opening at the distal tip portion of said catheter body, said opening in fluid communication with said infusion lumen for infusion of treated fluids into the vessel.

8. The catheter of claim 7, wherein the at least one infusion port further comprises at least one side port in fluid communication with said infusion lumen for infusion of treated fluids into the vessel.

9. The catheter of claim 1, wherein a bottom surface of the catheter body and a bottom surface of the manifold are aligned with one another such that the proximal end of the catheter body is configured to lie flat against a surface.

10. The catheter of claim 1, wherein a cross-sectional shape of each of the first and second withdrawal lumens comprises a crescent.

11. The catheter of claim 1, wherein at least one of the first and second withdrawal lumens extends distally beyond a corresponding one of the plurality of withdrawal ports and comprises a closed distal end and a filler material disposed within said at least one of the first and second withdrawal lumens between said corresponding withdrawal port and said closed distal end.

12. A multi-lumen catheter for use in the extracorporeal treatment of bodily fluids with an extracorporeal treatment unit, comprising:
 a catheter body having a length disposed about a longitudinal axis, said catheter body having a plurality of withdrawal ports and at least one infusion port disposed along said catheter body length,
 said catheter body having first and second withdrawal lumens for transport of bodily fluids withdrawn from a body vessel to said extracorporeal treatment unit, each withdrawal lumen in fluid communication with at least one of said withdrawal ports, an infusion lumen in fluid communication with the at least one infusion port, said infusion lumen extending longitudinally along said catheter body length for transport of treated fluids from said extracorporeal treatment unit into the body vessel through said at least one infusion port, wherein the infusion lumen is disposed substantially at the center of said catheter body about said longitudinal axis, said first withdrawal lumen extending longitudinally adjacent said infusion lumen along said catheter body length, and said second withdrawal lumen extending longitudinally adjacent said infusion lumen along said catheter body length, and
 a molded manifold coupled to a proximal end of said catheter body, the manifold configured to include a merger of the first and second withdrawal lumens into a single withdrawal lumen, the manifold comprising an infusion inlet port, an infusion outlet port coupled to the infusion lumen, and an infusion conduit coupled between the infusion inlet port and the infusion outlet port, each of the infusion inlet port and the infusion outlet port being axially aligned with the longitudinal axis of the catheter body.

13. The catheter of claim 12, wherein said withdrawal lumens are disposed at opposite sides of said infusion lumen.

14. The catheter of claim 12, wherein said manifold includes a withdrawal outlet port, a withdrawal inlet port coupled to each of the withdrawal lumens, and a withdrawal conduit coupled to each withdrawal inlet port, being angled vertically and horizontally toward the center of said catheter body such that the withdrawal conduits intersect to form a single conduit leading to the withdrawal outlet port for transport of bodily fluids withdrawn from the body vessel to said extracorporeal treatment unit.

15. The catheter of claim 14, wherein the infusion inlet port coupled to the infusion conduit and the withdrawal outlet port coupled to the single conduit of the withdrawal conduit are in vertical alignment, and wherein the infusion outlet port coupled to the infusion lumen and the withdrawal inlet ports coupled to the withdrawal lumens are in horizontal alignment, and the withdrawal inlet ports are disposed at opposite sides of the infusion outlet port coupled to the infusion lumen.

16. The catheter of claim 14, further comprising a withdrawal extension tube coupled to the withdrawal outlet port of the manifold for transport of bodily fluids to said extracorporeal treatment unit, and an infusion extension tube coupled to the infusion inlet port of the manifold for transport of treated fluids from said extracorporeal treatment unit.

17. A method for treating a body fluid of a body vessel, comprising:
 inserting a distal end of a catheter into said vessel, the catheter having a body of a length, said catheter body having a plurality of withdrawal ports and at least one infusion port disposed along said catheter body length, said catheter body having first and second withdrawal lumens, each withdrawal lumen in fluid communication with at least one of said withdrawal ports, the first and second withdrawal lumens merge along a portion of said catheter body proximal to said withdrawal ports, and an infusion lumen in fluid communication with the at least one infusion port, said infusion lumen extending longitudinally along said catheter body length, wherein the infusion lumen is disposed substantially at the center of said catheter body, said first withdrawal lumen extending longitudinally adjacent said infusion lumen along said catheter body length, and said second withdrawal lumen extending longitudinally adjacent said infusion lumen along said catheter body length;
 withdrawing body fluid to be treated from said vessel through said withdrawal ports;
 transporting said withdrawn fluid through said withdrawal lumens and through a withdrawal conduit of a manifold disposed at a proximal end of said catheter body to a treatment instrument, wherein said manifold is configured to include the merger of the first and second withdrawal lumens;
 treating said fluid in said treatment instrument;
 transporting said treated fluid from said treatment instrument through an infusion conduit of said manifold and through said infusion lumen, wherein the infusion conduit and the infusion lumen are coaxial with one another along a longitudinal axis of said catheter; and
 infusing treated fluid into said body vessel through the at least one infusion port.

18. The method of claim 17, wherein said withdrawal lumens are disposed at opposite sides of said infusion lumen.

19. The method of claim 18, wherein each of the first and second withdrawal lumens has a cross-sectional area sized to permit sufficient fluid flow rate for continuous extracorporeal treatment without stoppage.

20. The method of claim 17, wherein said treatment instrument comprises a dialyzer.

* * * * *